US00PP23121P2

(12) United States Plant Patent
Kordes

(10) Patent No.: US PP23,121 P2
(45) Date of Patent: Oct. 23, 2012

(54) FLORIBUNDA ROSE PLANT NAMED 'KORBUROX'

(50) Latin Name: *Rosa hybrida*
Varietal Denomination: KORburox

(75) Inventor: Tim-Hermann Kordes, Klein Offenseth-Sparrieshoop (DE)

(73) Assignee: W. Kordes' Söhne-Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 13/135,853

(22) Filed: Jul. 15, 2011

(51) Int. Cl.
*A01H 5/00* (2006.01)

(52) U.S. Cl. ..... Plt./142

(58) Field of Classification Search ..... Plt./142
See application file for complete search history.

*Primary Examiner* — Annette Para

(57) ABSTRACT

A new and distinct variety of rose with long lasting, novel dark red and white flowers, and attractive foliage with excellent disease resistance. It exhibits moderate growth with an compact and arching habit with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORburox'.

CROSS REFERENCES AND FEDERAL R&D STATEMENT

There are no cross referenced or related applications. This variety was developed without the aid of any research grant.

The new variety of rose plant of the present invention originated from a controlled crossing in a breeding program of two distinct parents during the summer of 1999. The crossing was between an 'un-named seedling' and an 'un-named seedling'.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORburox'.

SUMMARY OF THE INVENTION

The new rose plant may be distinguished from its seed parent, an 'un-named seedling', by the following combination of characteristics:

1. The flowers of 'KORburox' are dark red and white colored, while the flower color of the seed parent is pink.
2. The petal count of 'KORburox' is double while the petal count of the seed parent is semi-double.

The new rose plant may be distinguished from its pollen parent, an 'un-named seedling' by the following combination of characteristics:

1. The flowers of 'KORburox' are dark red and white colored, while the flower color of the pollen parent is dark red.

2. The disease resistance of 'KORburox' is excellent while the disease resistance of the pollen parent is less than average.

The objective of the hybridization was to create a new and distinct rose plant with unique qualities, such as:

1. Uniform growth and flowering;
2. Abundant attractive, recurrent flowers;
3. Attractive and abundant foliage; and
3. Resistance to diseases encountered in landscapes and gardens.

This combination of qualities is not present in prior rose cultivars known to the inventor. These objectives have been substantially achieved and in that distinguish 'KORburox' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORburox' was selected in May, 2000 from the seedling beds to be asexually propagated for further evaluation. The first asexual propagation of 'KORburox' was done by budding to seedling understocks in July, 2000 at the inventor's nursery in Offenseth-Sparrieshoop, Germany.

This initial and other subsequent propagations conducted in controlled environments demonstrate that 'KORburox' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORburox'.

DETAILED BOTANICAL DESCRIPTION

The following is a description of 'KORburox', as observed growing in July, 2011 in a nursery in Jackson County, Oreg. on plants of 2 years of age. Color references are made using The Royal Horticultural Society (London, England) Colour Chart, 2001 except where common terms of color are used.

For a comparison, several physical characteristics of the rose variety 'KORplunblo', a non-patented rose variety from the same inventor are compared to 'KORburox' in Chart 1.

CHART 1

| Characteristic | 'KORburox' | 'KORplunblo' |
|---|---|---|
| Flower colors: | Dark red and white. | Orange red and white. |
| Fragrance: | Light. | None. |
| Foliage: | Darker green and more abundant. | Lighter green and less abundant. |

Parents:

*Seed parent*.—An 'un-named seedling'.

*Pollen parent*.—An 'un-named seedling'.

Classification:

*Botanical classification*.—*Rosa hybrida* 'KORburox'.

*Commercial classification*.—Floribunda rose.

FLOWER AND FLOWER BUD

Blooming habit: Recurrent.

Flower bud:

*Size*.—Upon opening, 30 mm in length from base of receptacle to distal end of bud and 25 mm diameter at its widest point.

*Bud form*.—Short. Broad based.

*Bud color*.—As sepals first unfold, bud color is White Group N155B, with petal edges Red-Purple Group N157B. When ¼ open, the upper surface of petals is White Group N155B and the lower surface is Red-Purple Group 161C.

*Sepals*.—Color: Upper surface Green Group 143D. Lower surface Yellow-Green Group 144D, with intonations of Greyed-Red Group 182C. Size: Average 20 mm long×8 mm wide. Shape: Triangular. Sepals generally subulate. Weak foliaceous appendages on three of the five sepals. Apex: Apiculate. Base: Flat at union with receptacle. Quantity: Five. Surface texture: Upper side: Pubescent. Lower surface: Pubescent with stipitate glands. Margins: Pubescent with stipitate glands.

Receptacle:

*Surface*.—Smooth, shiny.

*Color*.—Yellow-Green Group 144A.

*Shape*.—Funnel-shaped.

*Size*.—15 mm (h)×5 mm (w).

Peduncle:

*Surface*.—With moderate numbers of stipitate glands.

*Length*.—20 to 35 mm average length.

*Diameter*.—2 to 3 mm average diameter.

*Color*.—Yellow-Green Group 144B.

*Strength*.—Moderately strong.

*Borne*.—Multiple flower buds per stem, generally 2 to 5.

Flower bloom:

*Fragrance*.—Light.

*Duration*.—On the plant 4-6 days. As a cut flower, 3-4 days. Senesced petals drop away cleanly.

*Size*.—Medium. When open, the average flower diameter is 40 mm and the average flower height is 25 mm.

*Form*.—Shape of flower when viewed from the side: Upon opening, upper part: Flat. Upon opening, lower part: Flattened convex. Open flower, upper part: Flat. Open flower, lower part: Flattened convex.

Color:

*Upon opening, petals*.—Outermost petals: Outer Side: White Group N155B. Inner Side: Red-Purple Group N57B.

*Innermost petals*.—Outer Side: Red-Purple Group 65D. Inner Side: Red-Purple Group 57A.

*Upon opening, basal petal spots*.—Basal petal spot, outermost petals: Outer Side: White Group 155B. Inner Side: White Group 155D. Basal petal spot, innermost petals: Outer Side: White Group 155B. Inner Side: White Group 155C.

*After opening, petals*.—Outermost petals: Outer Side: Basal zone is White Group 155C. The middle and marginal zones range from Red Group 55C to 55D. Inner Side: Basal zone is White Group 155C. The middle and marginal zones are Red Group 53C. Innermost petals: Outer Side: Basal zone is White Group 155C. The middle and marginal zones Red Group 56C. Inner Side: Basal zone is White Group 155C. The middle and marginal zones are Red Group 56D.

*After opening, basal petal spots*.—Basal petal spot, outermost petals: Outer Side: White Group 155B. Inner Side: White Group 155C. Basal petal spot, innermost petals: Outer Side: White Group 155B. Inner side: White Group 155B.

General tonality: On open flower Red Group 53B. No change in the general tonality at the end of the $5^{th}$ day. Afterwards, general tonality is Red Group 53D.

Petals:

*Petal count*.—Double. Average Range: Approximately 25 petals under normal conditions.

*Petal reflex*.—Petals reflex somewhat.

*Petal edge*.—Ruffled.

*Petal shape*.—Obovate. Apex shape is round. Shape of base is deltoid.

*Petal size*.—25-30 mm (l)×20-25 mm (w).

*Thickness*.—Thin.

*Petal arrangement*.—Not formal.

Petaloids:

*Petaloid count*.—Average of 2-5 per flower.

*Petaloid size*.—Petaloids are 8-10 mm (l)×2-4 mm (w).

*Petaloid color*.—Color of inner side is Red Group 53C. Color of outer side is Red Group 56D.

*Petaloid texture*.—Thick.

*Margins*.—Undulated.

*Petaloid shape*.—Most commonly deltoid, with some petaloids highly irregular. Apex: Deltoid. Base: Pointed.

Reproductive organs:

*Pistils*.—Average. Approximately 25 present. Stigmas: Location: Slightly superior in position to anthers. Color: Green-Yellow Group 1D. Styles: Length: 8-9 mm long, on average. Color: Yellow-Green Group 144C.

*Stamens*.—Approximately 35 on average and regularly arranged. Anthers: Size: Average 1 mm long. Pollen: Present. Color: Greyed-Orange Group 163A. Filaments: Color: Yellow-Green Group N 144. Length: 3-4 mm.

THE PLANT

Growth: Moderately vigorous.

Plant habit: Compact and arching habit. When grown as a field grown plant, the average plant height is 60 cm and the average plant width is 50 cm.

Blooming: Floriferous.

Stems:

*Stem color*.—Young wood: Yellow-Green Group 144D. Older wood: Yellow-Green Group 144C.

*Stem surface*.—Young wood: Smooth. Older wood: Smooth.

Prickles: Absent.

Leaves and leaflets: Normally 5 leaflets on normal leaves in middle of the stem.

*Venation pattern*.—Pyramidal net pattern.

*Leaf size*.—145 mm (l)×110 mm (w).

*Abundance*.—Average.

*Texture*.—Thin. Upper side of leaflet: Semi-glossy. Smooth. Under side of leaflet: Matte. Smooth.

*Color, mature foliage*.—Upper Leaf Surface: Yellow-Green Group 146A to 146B. Lower Leaf Surface: Yellow-Green Group 146D.

*Color, juvenile foliage*.—Upper Leaf Surface: Yellow-Green Group 144A. Lower Leaf Surface: Yellow-Green Group 146D.

*Anthocyanin intonation*.—Present. Intonations of Greyed-Purple Group 183C present on juvenile leaflets and margins.

Stipules:

*Size*.—On average 15 mm (l) and 4 mm from distal tip to distal tip.

*Stipule color*.—Yellow-Green Group 146D.

*Anthocyanin*.—Greyed-Purple Group 183B.

*Stipitate glands*.—Present on margins.

*Shape*.—Apex: Apiculate. Base: Flat.

Petiole:

*Length*.—Average 20-25 mm.

*Diameter*.—Average 2 mm.

*Petiole color*.—Yellow-Green Group 146C.

*Underneath*.—Occasional prickle, slightly pubescent.

*Margins*.—With stipitate glands.

*Anthocyanin*.—Greyed-Red Group 184C.

Petiole rachis:

*Length*.—Average 20-30 mm.

*Diameter*.—Average 2 mm.

*Color*.—Yellow-Green Group 146C.

*Underneath*.—Prickles at leaflet attachment and fine pubescence.

*Margins*.—Slightly pubescent with limited numbers of stipitate glands.

Leaflets:

*Size*.—Average size of the terminal leaflet is 60-65 mm (l)×40 mm (w).

*Shape*.—Base: Ovate. Apex: Ovate

*Margins*.—Finely serrated.

*Surface*.—Upper: Glossy. Under: Matte.

*Texture*.—Thin.

*Arrangement*.—Pinnate.

*Venation*.—Reticulate.

Hips/seed formation: None observed.

Winter hardiness: To date, the variety has been grown successfully in Zones 5-9.

Disease resistance: Excellent resistance to Powdery mildew (*Sphaerotheca pannosa*), blackspot (*Diplocarpon rosae*), and rust (*Phragmidium* sp.) diseases under normal growing conditions.

I claim:

1. A new and distinct variety of rose plant, as described and illustrated herein.

* * * * *

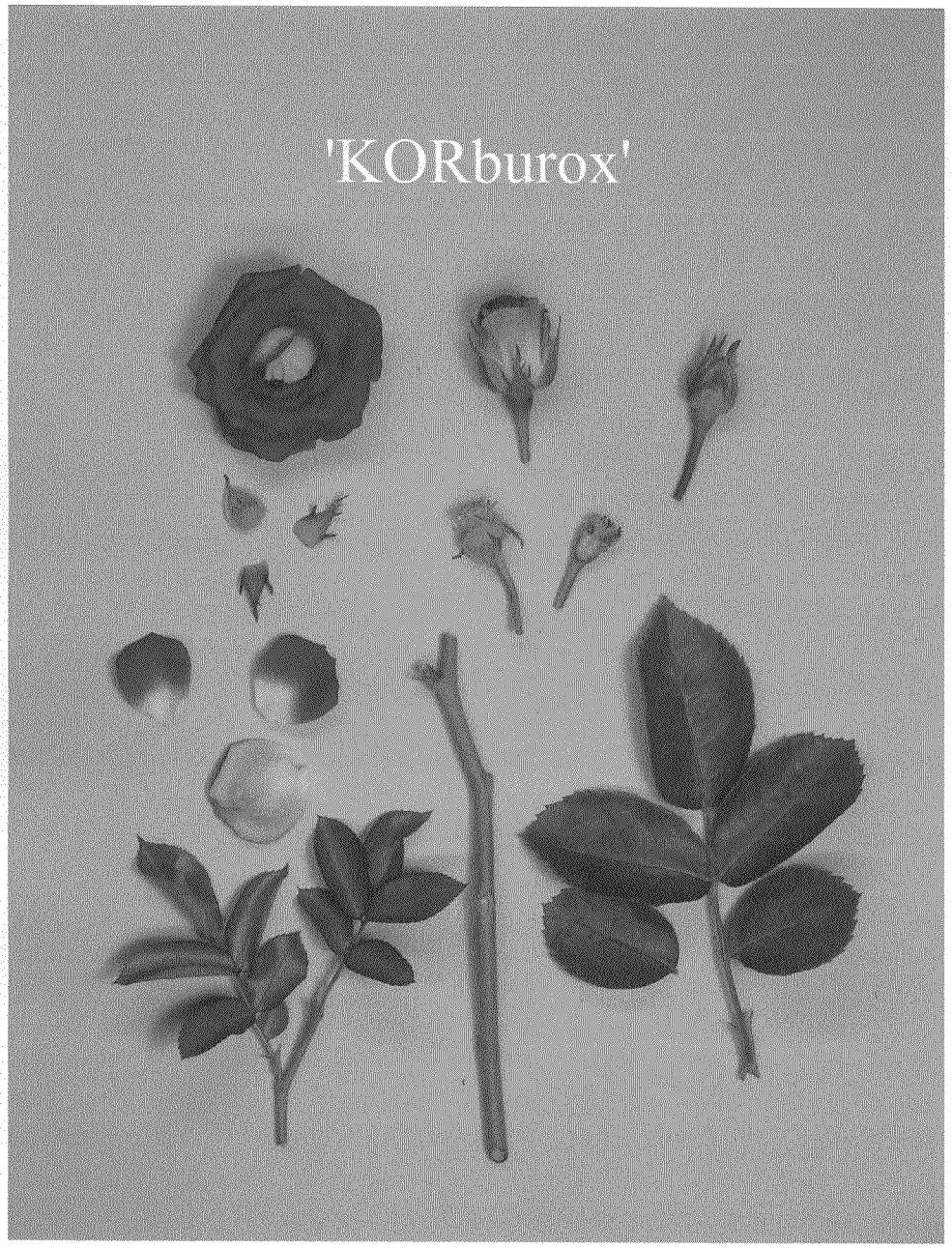
'KORburox'